United States Patent [19]

Reardan et al.

[11] Patent Number: 5,059,413

[45] Date of Patent: Oct. 22, 1991

[54] SCINTIGRAPHIC MONITORING OF IMMUNOTOXINS USING RADIONUCLIDES AND HETEROBIFUNCTIONAL CHELATORS

[75] Inventors: Dayton Reardan, Hercules; Susan Bernhard, San Francisco, both of Calif.

[73] Assignee: Xoma Corporation, Berkeley, Calif.

[21] Appl. No.: 182,673

[22] Filed: Apr. 18, 1988

[51] Int. Cl.$^5$ .................... A61K 49/02; A61K 39/395
[52] U.S. Cl. ........................................ 424/4.1; 534/14; 530/391; 530/402
[58] Field of Search ............................ 424/1.1; 534/14; 530/391, 402

[56] References Cited

U.S. PATENT DOCUMENTS

| | | | |
|---|---|---|---|
| 4,479,930 | 10/1984 | Hnatowich | 424/1.1 |
| 4,622,420 | 11/1986 | Meares et al. | 562/443 |
| 4,624,846 | 11/1986 | Goldenberg | 424/1.1 |
| 4,708,862 | 11/1987 | Baldwin | 424/1.1 |

OTHER PUBLICATIONS

Halpern, S.E., et al., "Stability, Characterization, and Kinetics of $^{111}$In-labeled Monoclonal Antitumor Antibodies in Normal Animals and Nude Mouse-Human Tumor Models," *Cancer Research*, 43:5347-5355 (November 1983).

Pimm, M.V., "Immunoscintigraphy: Tumour Detection with Radiolabelled Antitumor Monoclonal Antibodies," (eds) V.S. Byers and R.W. Baldwin, MTP Press Ltd., Lancaster, PP. 21-43 (1987).

Ford, C.H.J., "Localisation and toxicity study of a vindesine-anti-CEA conjugate in patients with advanced cancer," *Br. J. Cancer*, 47:035-042 (1983).

Perkins, A.C., et al., "In Vivo Imaging of a Monoclonal Antibody Drug Conjugate (791T/36-Methotrexate): Experimental and Clinical Studies," In: Fourth Hamburg Symposium uber Tumormarker. (eds) H. Greten and R. Klapden, Georg Thieme Verlag Stuttgart, pp. 553-562 (1988).

Byers, V.S., et al., "Biodistribution of Ricin Toxin A Chain-Monoclonal Antibody 791T/36 Immunotoxin and Influence of Hepatic Blocking Agents," *Cancer Research*, 47:5277-5283 (October 15, 1987).

Perkins, A.C., et al., "Demonstration of the Hepatic Uptake of Radiolabelled Immunotoxins Using Gamma Scintigraphy," *Eur. J. Cancer Clin. Oncol.*, Vol. 23, No. 8, pp. 1225-1227 (1987).

Ballantyne, K.C., "Biodistribution of a Monoclonal Antibody-Methotrexate Conjugate (791T/36-MTX) in Patients with Colorectal Cancer," *Int. J. Cancer: Supplement 2*, 103-108 (1988).

*Primary Examiner*—John S. Maples
*Attorney, Agent, or Firm*—Townsend and Townsend

[57] ABSTRACT

This invention relates to an improved method for conducting scintigraphy to monitor of immunotoxins under clinical conditions. The improvement relates to the use of heterobifunctional chelators to bind radionuclides exclusively to the cytotoxic moiety of an immunotoxin.

23 Claims, 5 Drawing Sheets

SCINTIGRAPHIC MONITORING OF IMMUNOTOXINS USING RADIONUCLIDES AND HETEROBIFUNCTIONAL CHELATORS

BACKGROUND OF THE INVENTION

1. Field of the Invention

This invention relates to an improved method for conducting scintigraphy to monitor immunotoxins under clinical conditions. The improvement relates to the use of heterobifunctional chelators to bind radionuclides exclusively to the cytotoxic moiety of an immunotoxin.

2. Information Disclosure

The localization of radiolabelled monoclonal antibodies in tumours has been described (Halpern, S.E., Et Al: Stability, Characterization and Kinetics of $^{111}$In-labelled monoclonal antitumor antibodies in normal animals and nude mouse-human tumor models. Cancer Res., 43, 5355, 1983). Using radiolabels appropriate for gamma camera imaging, such as radioiodines ($^{131}$I or 123I) or radiometals ($^{111}$In or $^{99m}$Tc), monoclonal antibodies have been evaluated for imaging primary and recurrent malignant disease (Reviewed in Pimm, M.V. Immunoscintigraph: Tumour detection with radiolabelled antitumour antibodies. In: Immunology of Malignant Diseases. (eds) V.S. Byers and R.W. Baldwin, MTP Press Ltd., Lancaster, pp 21–43, 1987).

The scintigraphic expertise developed with radiolabelled antibodies can be used to examine the biodistribution of immunoconjugates; however, to date there has been little work in this field. Ford, et al., (Localization and toxicity study of a vindesine-anti-CEA conjugate in patients with advanced cancer. Br. J. Cancer, 47, 35–42, 1983) imaged the biodistribution and tumour localization of $^{131}$I-I-labelled vindesine-antiCEA polyclonal antibody conjugate. Perkins, et al., (In vivo imaging of a monoclonal antibody drug conjugate (791T/36-Methotrexate): Experimental and Clinical Studies. In: Fourth Hamburg Symposium uber Tumormarker. (eds) H. Greten and R. Klapden, Georg Thieme Verlag Stuttgart, pp 559–562, 1988) carried out similar studies with a $^{131}$I-labelled monoclonal antibody-methotrexate conjugate in patients with colorectal cancer. These procedures have, however, only imaged the distribution of the antibody part of the conjugate without formal proof that the distribution of the drug paralleled that of the antibody. Direct observation of drug distribution has been limited by the difficulty in radiolabelling drugs with sufficient specific activity to permit external detection.

In the case of conjugates of antibody with protein toxins such as ricin toxin A chain (RTA) it is feasible to prepare conjugates in which either the whole molecule, or only the RTA or antibody moieties are radiolabelled, or even in which each component is independently labelled with a different radionuclide (Byers, et al., Biodistribution of ricin toxin A chain monoclonal antibody 791T/36 immunotoxin and the influence of hepatic blocking agents. Cancer Res., 47, 5277–5282, 1987). Preliminary studies on the imaging of the biodistribution in mice of RTA-monoclonal antibody 791T/36 conjugates in which only the RTA was labelled with $^{131}$I have also been reported. (Perkins, et al. Demonstration of the hepatic uptake of radiolabelled immunotoxins using gamma scintigraphy. Eur. J. Cancer Clin. Oncol., 23, 1225–1227, 1987).

BRIEF DESCRIPTION OF FIGURES AND TABLE

Table I. Biodistribution of $^{111}$In.

SUMMARY OF THE INVENTION

This invention provides methods for in vivo radioimmunodetection of cytotoxic immunotoxins which comprises the administration to a mammal of a radiolabeled immunotoxin having the radiolabel attached to the cytotoxic portion of the immunotoxin through a heterobifunctional chelator. It is preferred that the radiolabel is a radionuclide that emits either beta particles or gamma rays with gamma rays being preferred. The most preferred gamma emitting radionuclides are $^{99}$Tc or $^{111}$In.

The heterobifunctional chelators are used to link the radiolabel to the cytotoxic portion of the immunotoxin. These chelators are comprised of a first chelating portion and a second reactive portion which binds to the cytotoxin. Preferred heterobifunctional chelators are cyclic dianhydride of diethylenetriaminepentaacetic acid, and bromoacetamidobenzylethylenediaminetetraacetic acid.

These immunotoxins can be directed against any antigenic material in a biological host. Preferably the immunotoxins are diagnostic or therapeutic pharmaceuticals which are directed against various disease states. Such disease states would of necessity have an predetermined epitope which serves as a marker for the disease. These marker epitopes are either associated with or correlated with the existence of a particular disease or the quantity the marker is correlated with a disease state. More particularly the method of this invention embraces immunotoxins wherein the immunoglobulin component is specific for epitopes upon cell surface antigens wherein the epitopes are markers for a disease state. The preferred disease state is cancer for which numerous markers have been discovered. Most preferred are epitopes located upon the 72,000 dalton cell surface glycoprotein associated with osteogenic sarcoma derived cells such as the epitope bound by the antibodies secreted by the hybridoma line ATCC HB 9173 and epitopes located upon the carcinogenic embryonic antigen such as the epitope bound to by the antibodies secreted by the hybridoma line ATCC HB 9174.

Preferred cytotoxins include toxic lectins and their derivatives, daunomycin, adriamycin, methotrexate and cytarabine.

In addition to the above methods, this invention provides for imaging agents comprising a radio-labelled immunotoxin having the radiolabel attached through a heterobifunctional chelator to the cytotoxic portion of the immunotoxin. The preferred imaging agents are as described for the methods above.

DETAILED DESCRIPTION

This invention provides for an improved method for monitoring the biodistribution of immunotoxins during therapy for various disease conditions. By localizing the imaging label to the cytotoxic portion of the conjugate, one can ensure that the scintigraphy data one is obtaining correlates more precisely with the delivery of the therapeutic agent (toxin) than using the prior art methodology wherein the label is randomly distributed on both the immunoglobulin and the toxin portion of the conjugate or to the immunoglobulin alone.

The use of heterobifunctional chelators enables the clinician to customize his immunotoxin monitoring by choosing the most effective or convenient radionuclide including those with relatively short halflives.

A. The preparation of immunotoxins.

The imaging agents useful in this invention are comprised of an antigen binding component and a radiolabelled cytotoxin. The antigen binding component is typically an immunoglobulin. For this invention the term "immunoglobulin(s)" embraces polyclonal antibodies, monoclonal antibodies, reactive fragments thereof, such as Fv, Fab, F(ab)$_2$, synthetic immunoglobulins and recombinant immunoglobulins including chimeric immunoglobulins or their derivatives. Preferably, the immunoglobulins are MoAbs of the IgM or IgG isotype of murine, human or other mammalian origin.

The antigens that are typically targeted are those that are unique for a particular disease state. Most preferably the antigens are bound to a cell surface and are not readily shed into the patient's circulatory system. These antigens include proteins, glycoproteins, lipoproteins, polysaccharides and the like, which are produced by or displayed by the cells in response or as a result of the particular disease state. It should be understood that the immunoglobulin recognizes only a small portion of the antigen (epitopes) and that there may be normal antigens that have regions similar to the disease related antigen. Therefore this invention is specifically drawn to disease-related-epitopes on antigens which reflect the existence or localization of a disease state. It should be further recognized that this invention is useful where either the presence or absence of a disease-related epitope is indicative of the health condition of a patient or where a quantitative measurement of the disease-related epitope is determinative of the patient's condition. Examples of disease related antigens include the 72,000 dalton cell surface antigen associated with cells arising from osteogenic sarcomas (Cancer Res. 47:5277–5283, 1987), and the carcinoembryonic antigen (JNCI 69:799–805, 1982). Two hybridoma lines suitable for use in this invention have been deposited under the terms of the Budapest Treaty with the American Type Culture Collection (ATCC), Rockville, MD, U.S.A. Hybridoma lines HB 9173 and HB 9174 were deposited on Aug. 16, 1986 secreting antibodies directed against the 72,000 dalton glycoprotein antigen of osteogenic sarcoma derived cells and the carcinoembryonic antigen, respectively.

The cytotoxic portion of the immmunotoxin is fatal to a cell when internalized. A variety of cytotoxic agents are suitable for use in immunotoxins. The cytotoxic agents contemplated by this invention can include a number of chemotherapeutic drugs, such as vindesine, antifolates (eg. methotrexate), anthrocyclines (eg. adriamycin), bleomycin, daunomycin, cytarabinine and cisplatinum; mytomycins; and cytotoxic proteins such as ribosomal inactivating proteins including, pokeweed antiviral protein, abrin and ricin (or their A-chains), diphtheria toxin, pseudomonas exotoxin A, etc. or their recombinant derivatives. See generally, "Chimeric Toxins", Olsnes and Pihl, Pharmac. Ther., 25:355–381 (1982), and "Monoclonal Antibodies for Cancer Detection and Therapy," eds. Baldwin and Byers, pp. 159–179, 224–266, Academic Press (1985), both of which are incorporated herein by reference.

Toxic lectins are of particular interest in this invention. The cytotoxic action of toxic lectins, and especially that of ricin and abrin, has been well studied. It is known that toxic lectins consist of two polypeptide chains, A and B, linked by means of disulfide bridge(s). Cytotoxicity is associated with the A chain and its inhibition of protein synthesis in nucleated cells. The B chain is essentially a delivery vehicle for the A chain. The B chain recognizes polysaccharide units at the surface of cells and creates a high affinity interaction with such units. Once the B chain binds with polysaccharide units at the cell surface, the A chain is incorporated into the cell, blocking ribosomal protein synthesis and ultimately leading to cell death. The use of ricin A chain is preferred in this invention.

Toxic lectins of similar structure and function as ricin include abrin, modeccin and mistletoe toxin. One other category of ribosomal inactivating protein (RIP) is the toxin with only one subunit having functional characteristics analogous to the ricin A chain. This type of RIP lacks cytotoxicity to the intact cell because of the inherent absence of a binding fragment analogous to ricin B chain. Examples of RIP's of this latter type include gelonin and pokeweed antiviral protein.

Accordingly, any toxic lectin which may be split into A and B polypeptide chains, specifically abrin, modeccin and mistletoe toxin may be used in the same way ricin is used in the example provided below. In addition, any RIP, specifically gelonin, pokeweed antiviral protein, may be used the same way as ricin A chain. Such materials are equivalents to the toxic lectin A chain for purposes of this invention.

The two components, cytotoxin and immunoglobulin, are complexed or chemically bonded together by any of a variety of well-known chemical procedures. For example, when the cytotoxic agent is a protein and the second component is an intact immunoglobulin, such as a monoclonal antibody, the linkage may be by way of carbodiimide, glutaraldehyde, heterobifunctional cross-linkers, e.g., N-succinimidyl 3-(2-pyridyldithio) propionate (SPDP), homobifunctional cross-linkers, e.g., bis-maleimide, cross-linking of proteins without exogenous cross-linkers by means of groups reactive to the individual protein such as carbohydrate, disulfide, carboxyl or amino groups via oxidation or reduction of the native protein, or treatment with an enzyme or the like. For non-protein cytotoxins the procedures will vary in accordance with the selected cytotoxin. For example, conjugation procedures are detailed in U.S. Pat. No. 4,631,190; Int. Natl. J. of Cancer 33:737–744 (1984); and EP 253,202. Production of various immunotoxins is well-known within the art, and general reviews can be found, for example, "Monoclonal Antibody-Toxin Conjugates: Aiming the Magic Bullet", Thorpe et al. Monoclonal Antibodies in Clinical Medicine, Academic Press, pp. 168–190 (1982). These references are each incorporated herein by reference.

B. The binding of radiolabels to the cytotoxic moiety.

According to the present invention, an immunotoxin of interest is labeled with a detectable label administered internally to a host for detection by external means. The external detection of a label internally localized at the site of infection in a host permits the non-invasive diagnosis of the anatomy, pathology and progress of such disease as well as a means of following the delivery of the therapeutic agent to the site of infection or pathology.

A variety of detectable labels and means for their detection are well known to those skilled in the art. These include, but are by no means limited to, tomography employing radio-opaque labels, NMR scanning employing paramagnetic labels, and scintigraphy employing radionuclides. While tomography and NMR scanning are currently problematic with respect to the subject methods (a situation that will undoubtably be remedied by advances in the art), scintigraphy using radionuclides as labels may be currently employed. The image obtained may be enhanced by computer, dual label subtraction, or the like.

A variety of radionuclides are available for use in scintigraphy including iodine-123 ($^{123}I$), iodine-125 ($^{125}I$), iodine-131 ($^{131}I$), technetium-99m ($^{99m}Tc$) gallium-67 ($^{67}Ga$), thallium-201 ($^{201}Tl$), phosphorus-32 ($^{32}P$), chromium-57 ($^{57}Cr$), and indium-111 ($^{111}In$) or other beta or gamma emitters. For the most part, the elemental nature of the radionuclide is not critical, however, the characteristics of the decay product will be of clinical importance. Such characteristics are subject to evaluation by the clinician and vary from patient to patient. For example, the useful energy of the radiation may vary from about 50 KeV to 350 KeV and the half life ($T_{\frac{1}{2}}$) from about several hours up to sixty days, or more. Radionuclides, such as iodine-131, yttrium-90, rhenium-188, and bismuth-212 are beta emitting radioimmunotherapeutic agents in addition to their ability to act as detectable labels.

The binding of label to the cytotoxic agent is typically accomplished with a heterobifunctional linking agent. The two functionalities will differ in accordance with the selected cytotoxin and label. Typically for cytotoxic proteins the binding functionality will be a reactive moiety able to covalently bind to thiol groups, free carboxyls or amines. Examples of such reactive moieties include activated acyl groups such as N-hydroxy succinimidyl (NHS) ester, arylazides, and alkyl halides, or α-haloacetamides such as α-bromoacetamide. More specifically haloacetamidobenzoyl where the halo moiety may be iodo-, bromo- or chloro- and 4-(N-maleimidomethyl-cyclohexane-1-carbonyl.

For coupling radionuclides to non-protein cytotoxic agents, one would utilize the same reactive groups found on proteins, eg. thiols, amines and carboxy groups.

The functionality for binding of the radiolabel will also vary in accordance with the selected isotope. For example, the preferred isotopes are metal ions which can be effectively chelated to a ligand having multiplicity of carboxylic acids. Examples of such chelators are diethylenetriaminepentaacetic acid (DTPA) derived from the cyclic anhydride described in U.S. Pat. No. 4,479,930 and bromoacetamidobenzylethylenediaminetetraacetic acid described in U.S. Pat. No. 4,622,420. Both patents being incorporated by reference herein.

The examples provided below offer details of a preferred embodiment wherein $^{111}In$ is bound through a preferred heterobifunctional chelator, DTPA. The $^{99}Tc$ label is also preferred and either DTPA or thiol chelators can be used to ligate this label to the chelator (see U.S. Pat. No. 4,444,690).

Details for coupling the heterobifunctional chelators to cytotoxic proteins are as used for standard coupling reactions known in the art for the coupling agents described above. The example provided below will give additional illustration of conjugation with heterobifunctional agents to proteins. The reaction conditions for non-protein cytotoxins are similar to those used to conjugate to similar moieties on proteins. By way of further illustration, methotrexate, which is a non-protein cytotoxin, has available amino groups and a two-step procedure is easily envisioned. First a DTPA labeling of amino groups on the methotrexate, and secondly, carbodiimide coupling of a carboxylic acid group on the methotrexate to an amino (lysine) group on the protein molecule. More specifically, DTPA labeling is carried out in a non-amine buffer (such as sodium phosphate) above pH 8.0. The DTPA will react with any good nucleophile on the drug moiety, in this case the aromatic amines on methotrexate. The DTPA-labeled drug is then purified to remove excess DTPA. The carbodiimide coupling reaction of the antibody to the DTPA-labeled methotrexate would be carried out in a nonamine buffer between pH 5.0 and 6.0.

C. The administration and monitoring of radiolabelled immunotoxins.

One of the distinct advantages of the disclosed invention is the possibility of preparing immunotoxin having the heterobifunctional chelator without the label. This would be a stable intermediate with a long shelf life. The clinician could readily select from a number of useful radionuclides that are commercially available.

After preparing the three components of the imaging agents of this invention, pharmaceutical formulations suitable for administration to patients must be prepared. Suitable carriers for the imaging agents include sterile, non-pyrogenic aqueous solutions. These solutions are preferably isotonic solutions buffered in the physiological range. Formulations may optionally include a preservative. Examples of preservatives include surfactants, particularly polysorbate 80, or the like. In addition, the preparation can be optionally lyophilized for long term storage.

Means for administering immunotoxins for therapeutic purposes and for administering immunoimaging agents for scintigraphy are known. U.S. Pat. No. 4,708,862. The precise proportion of labeled to unlabeled immunotoxin for following delivery of cytotoxin will vary in accordance with the size and condition of the patient as well as the choice of label. Typically not all of the immunotoxin will be labelled and appropriate calculation can be conducted to determine the efficacy of cytotoxic delivery by the immunoglobulin. A typical pharmaceutical composition for intravenous infusion could be made up to contain about 150 ml of normal saline and about 1 mg of labeled immunotoxin to about 30 mg unlabeled immunotoxin. Where rapid clearance of the immunotoxin is a problem due to the liver, inhibitors of hepatic clearance such as mannosylated human serum albumin may be added to the formulation.

The following examples are offered by way of illustration and are not to be viewed as limitations of this invention.

EXAMPLES

A. Preparation of DTPA - immunotoxin.

Conjugate of RTA30 and the monoclonal antibody 791T/36 was prepared in which the RTA moiety was modified with DTPA.

791T/36 antibody is an IgG2b murine monoclonal derived from osteogenicsarcoma immunization of mice. The hybridoma source is HB 9173 on deposit with the ATCC. The antibody was stored frozen ($-70°$ C.) in 5 mg aliquots in 0.1M Phosphate, 0.1M NaCl, pH 7.5. The ricin A chain (RTA30) used here was a single species (MW 30kD), referred to in the literature as $RTA_1$, (Biochem. Biophys. Acta 791, 341-348, 1982; Biochem. Biophys. Acta 840, 193-203, 1983; J. Cancer 36, 705-711, 1985; and J. Biol. Chem. 26, 5314-5219, 1986). The RTA30 was separated by ion exchange column chromatography, from a preparation of ricin A chain which occurs naturally as a mixture of two species, RTA30 (60-70%) and RTA33 (30-40%). The distinction is made because the difference between RTA30 and RTA33 is the extent of glycosylation; the pharmacokinetic properties of the two RTA species differ and appears to be influenced by carbohydrate composition.

The RTA30 was DTPA labelled an initial treatment with 50mM DTT (dithiothreitol) to reduce possible dimers. The RTA30 was then dialyzed, and free sulfydryls were protected with DTNB (dithionitrobenzoic acid). The protected RTA30 was equilibrated with 0.1M Na borate buffer, pH 8.7 by dialysis. A 0.014M stock solution of DTPA anhydride in DMSO was made and a ten-fold molar excess of DTPA was added to the RTA30-TNB (5 mg/ml). As determined by TLC Co-57 assay (Meares, et al Anal Biochem 142, 68-78, 1984), there were 0.64 DTPA groups per RTA. The DTPA-RTA30 was then treated with DTT to deprotect sulphydryls and equilibrated with 0.1M Na Phosphate, 0.1M NaCl, pH 7.5. The 791T/36 antibody (5 mg/ml) was treated with 15 fold molar excess of N-succinimidyl 3-(2-pyridyldithio) propionate (SPDP), using a 2 mg/ml SPDP stock prepared in ethanol. After 0.5h reaction at room temperature with stirring, excess SPDP was removed by dialysis. For the coupling reaction, 2.5 fold molar excess of RTA30 (2.2 mg) was added to PDP-antibody (4.2 mg) and the reaction was allowed to proceed at 4° C. overnight without stirring. The impure reaction mixture was applied to an AcA-44 (LKB) sizing column to remove free RTA30 and 2-thiopyridyl released during coupling. The reaction mixture can be treated to remove unreacted antibody.

Densitometry of a Coomassie stained 3-12% gradient SDS PAGE gel showed that free antibody comprised 21.5% of total protein. The gel showed that mono-, di- and tri-RTA30 conjugates were present in the reaction mixture, with an average of 1.3 RTA/antibody. An autoradiogram of radiolabelled DTPA-RTA30-791T/36 on SDS PAGE showed radioactivity associated only with the RTA-antibody conjugates. A trace (<5%) of free DTPA-RTA30 was detected on the autoradiogram. No labelled antibody band was detected. Antibody activity was assessed by the ability of the DTPA-RTA-immunotoxin to compete with fluorescein labelled 791T/36 antibody for binding to 791T cells (Robins, et al., J. Immunol. Meth., 90:344-348 (1986)). Activity was 74.3% compared with unmodified antibody. The amount of immunotoxin required to kill 50% of the cells in a tritiated thymidine uptake biological assay was 150 ng/ml.

B. $^{111}$In-labelling $^{111}$In-indium chloride (INS IP; Amersham International, Amersham, U.K.) (111 MBq in 0.2 ml) was mixed with an equal volume of 0.2 M pH 5.0 citrate buffer and added to 150 μl of DTPA-immunotoxin (approximately 1 mg). The mixture as incubated at room temperature for 15 min. and then passed through a 5.5×1.5 cm column of Sephadex G-25 (pre-packed PD10 column, Pharmacia, Sweden) with elution of 0.5 ml fractions with phosphate buffered saline (PBS). The fractions containing $^{111}$In were pooled.

C. Characterization of Radiolabelled Immunotoxin

Figure 1:
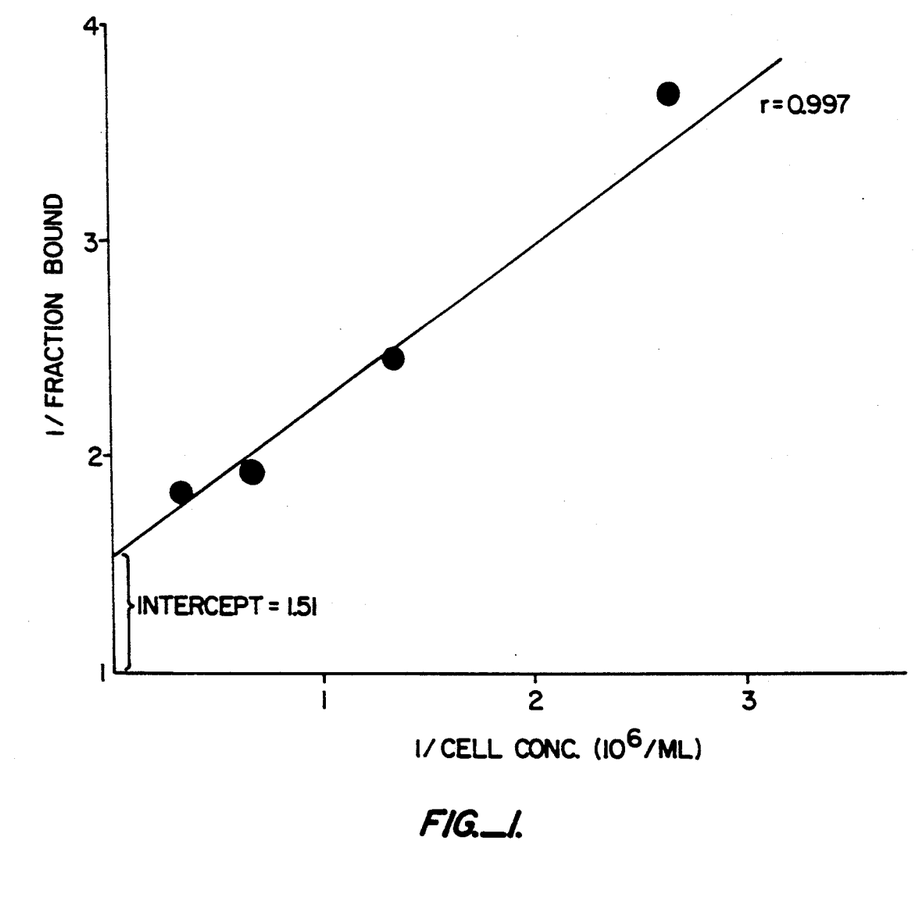
FIG. 1. Cell binding assay of $^{111}$In-DTPA-RTA-(791/36) to 791 positive cells.

Immunological activity of the preparation was determined by a binding assay with antigen positive (791T) cells and antigen negative (CoLo-205) cells. A constant amount of conjugate, $^{111}$In-DTPA-RTA-(791T/36), (100 ng in 1 ml) was incubated in replicates of three with a range of cell concentrations ($0.3-3 \times 10^6$ ml) for 4 hours at +4° C. with constant agitation. Cells were subsequently sedimented by centrifugation and the fraction of total radioactivity bound to the cell pellet determined. The analytical technique of Lindmo, et al., J. Immunol. Meth., 72:77-89 (1984), was used for data extrapolation to assess the proportion of $^{111}$In binding at a theoretical infinite cell concentration. In the cell binding test, 66% of the $^{111}$In bound to antigen positive 791T cells at extrapolation to infinite antigen excess (FIG. 1) but only 8% to antigen negative cells.

Figure 2:
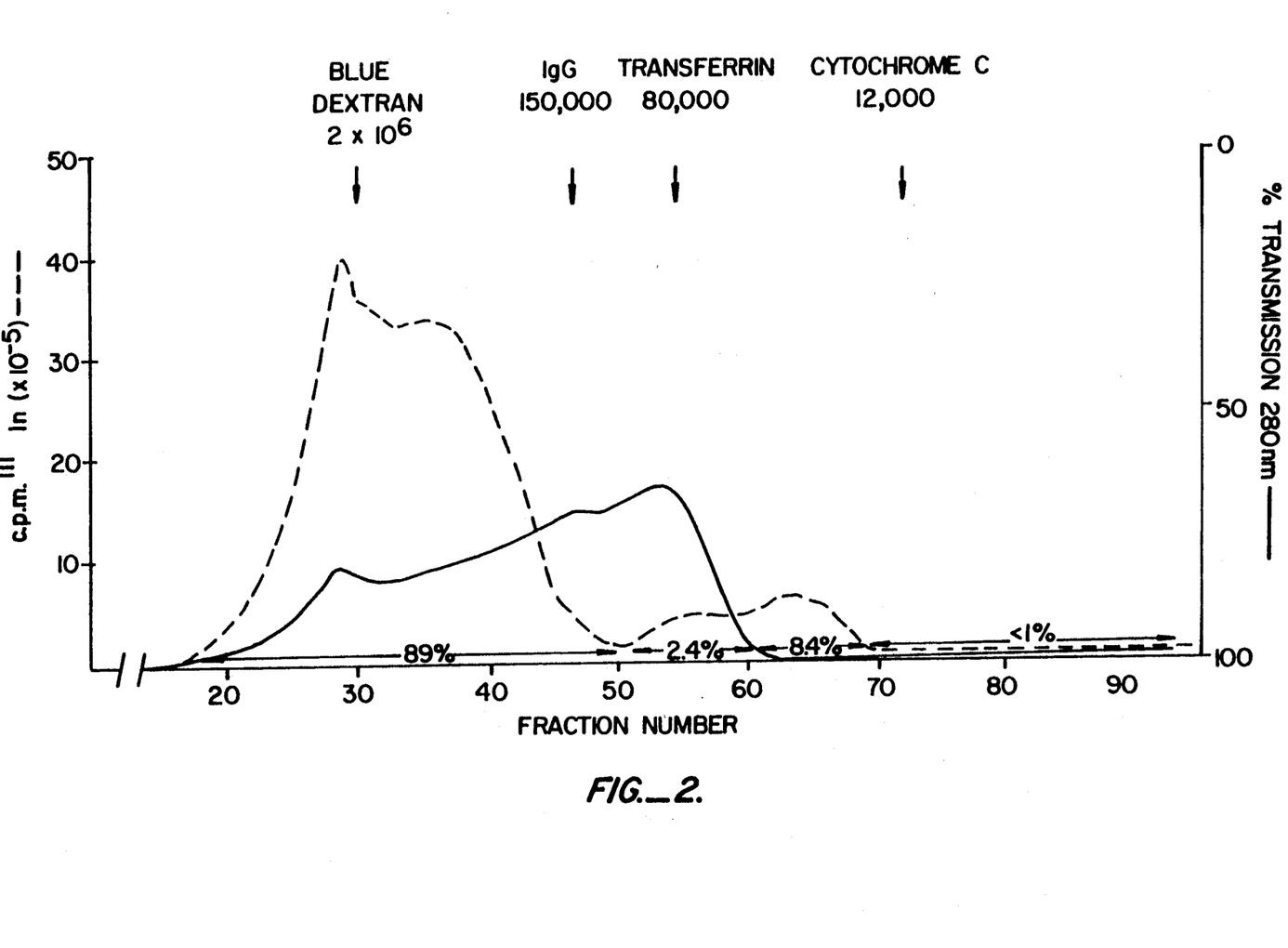
FIG. 2. The Chromatographic pattern of $^{111}$In-DTPA-RTA-(791/36) through Sephacryl S-300 after treatment with normal mouse serum.

The bound Indium was stable in normal mouse serum. The labeled conjugate was passed through Sephacryl S-300 (Pharmacia) gel filtration chromatography on a 90 cm×1.5 cm column and eluted in phosphate buffered saline (PBS) pH 7.2 (Perkins, et al., Eur. J. Nucl. Med., 10:296-301 (1985)) after addition of 50 μl of $^{111}$In-DTPA-RTA-(791T/36) to 1 ml of normal mouse serum. Protein in the eluate was continuously monitored by absorption of UV light at 280 nm, and 2 ml fractions were collected and assayed for $^{111}$In. The column had been pre-calibrated with an appropriate range of molecular weight markers (FIG. 2). $^{111}$In chelation efficiency was virtually 100%.

D. Biodistribution and Imaging Studies

Athymic nude mice (Olac, Oxon, U.K.) with xenografts of osteosarcoma 791T were used. A group of three mice with established tumour growths (approx. 1.5 cm diameter, mean weight 0.45 g) was injected intravenously with 50 μg (approximately 5 MBq) of $^{111}$Inlabelled immunotoxin. Serial imaging was carried out using an IGE Maxicamera II fitted with a pinhole collimator. In each case the mouse was anesthetized with ether to prevent movement while imaging and was placed prone beneath the collimator to provide a posterior view. Images were recorded for 2 minutes immediately post injection and at 4-6 and 24 h, using both photopeaks of In-111 (173 and 247 keV). Regions of interest (ROI) were drawn on the images around liver, kidneys and tumour and used to quantify the proportion of the whole body image count rate in these sites.

A further group of mice with similar size tumours (mean weight 0.49 g) was similarly injected and imaged but were also injected intraperitoneally with a preparation of mannosylated human serum albumin (MAN-HSA) at 200 mg/kg at $-$ 3 hr, 0 hr and $+$ 5 hr with respect to administration of labelled immunotoxin. The MAN-HSA had been prepared by the method of Monsigny, et al. in Biol. Cell, 51, 187-196, 1984.

Forty-eight hours after injection of labelled immunotoxin all mice were killed and dissected and $^{111}$In radioactivity assayed in weighed samples of blood, tumour, other organs and carcass.

Figure 3A:
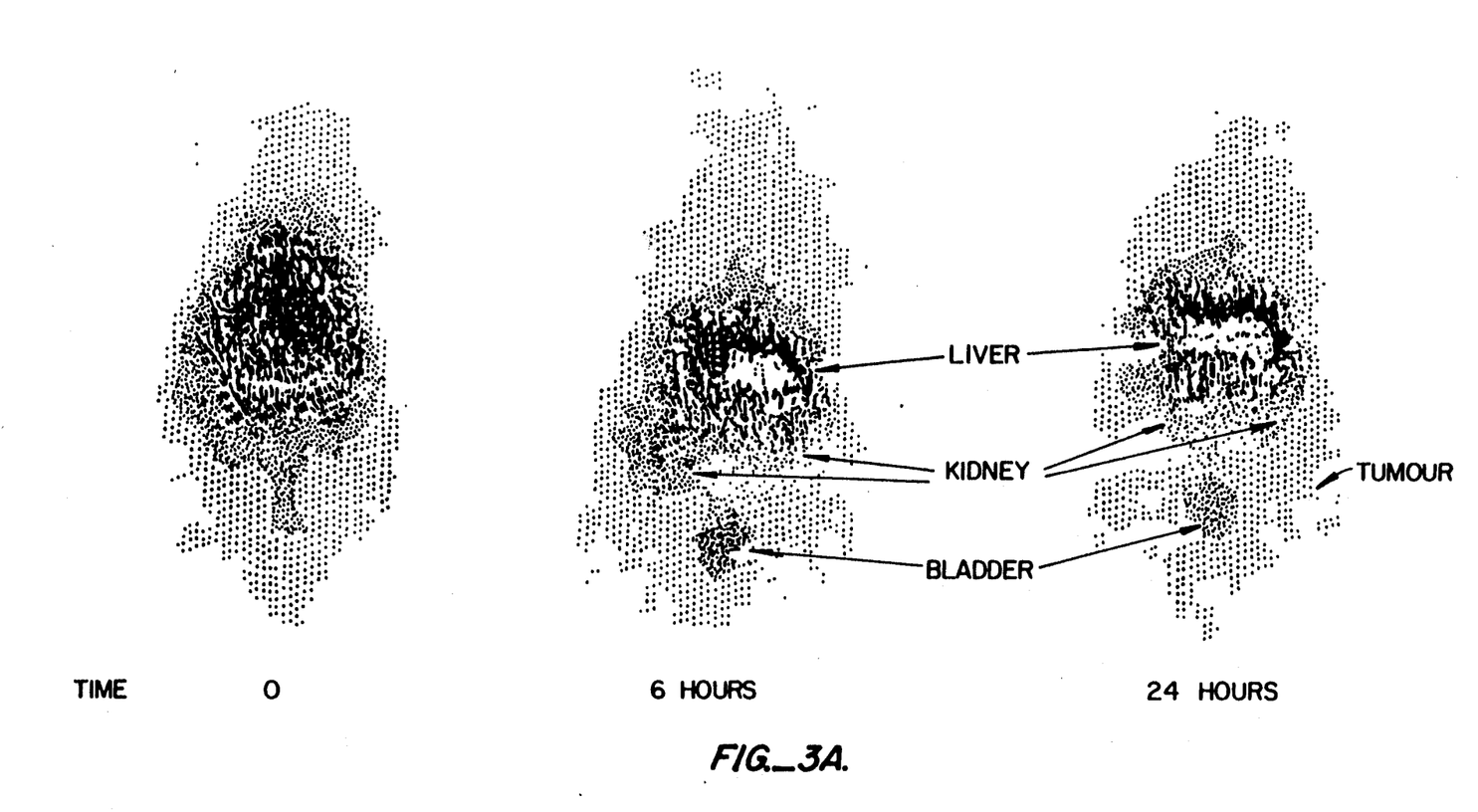
FIGS. 3a and 3b. Gamma camera imaging of mice with xenografts given $^{111}$In-DTPA-RTA-(791/36).

Gamma camera imaging of mice with xenografts given only $^{111}$In-immunotoxin showed rapid hepatic uptake of $^{111}$In (e.g., FIG. 3A). Some concentration of radioactivity in kidney and bladder was also seen by 6 hr and at 24 hr (FIG. 3A). Tumour localization of radiolabel was not clearly seen on the images of these mice.

Figure 3B:
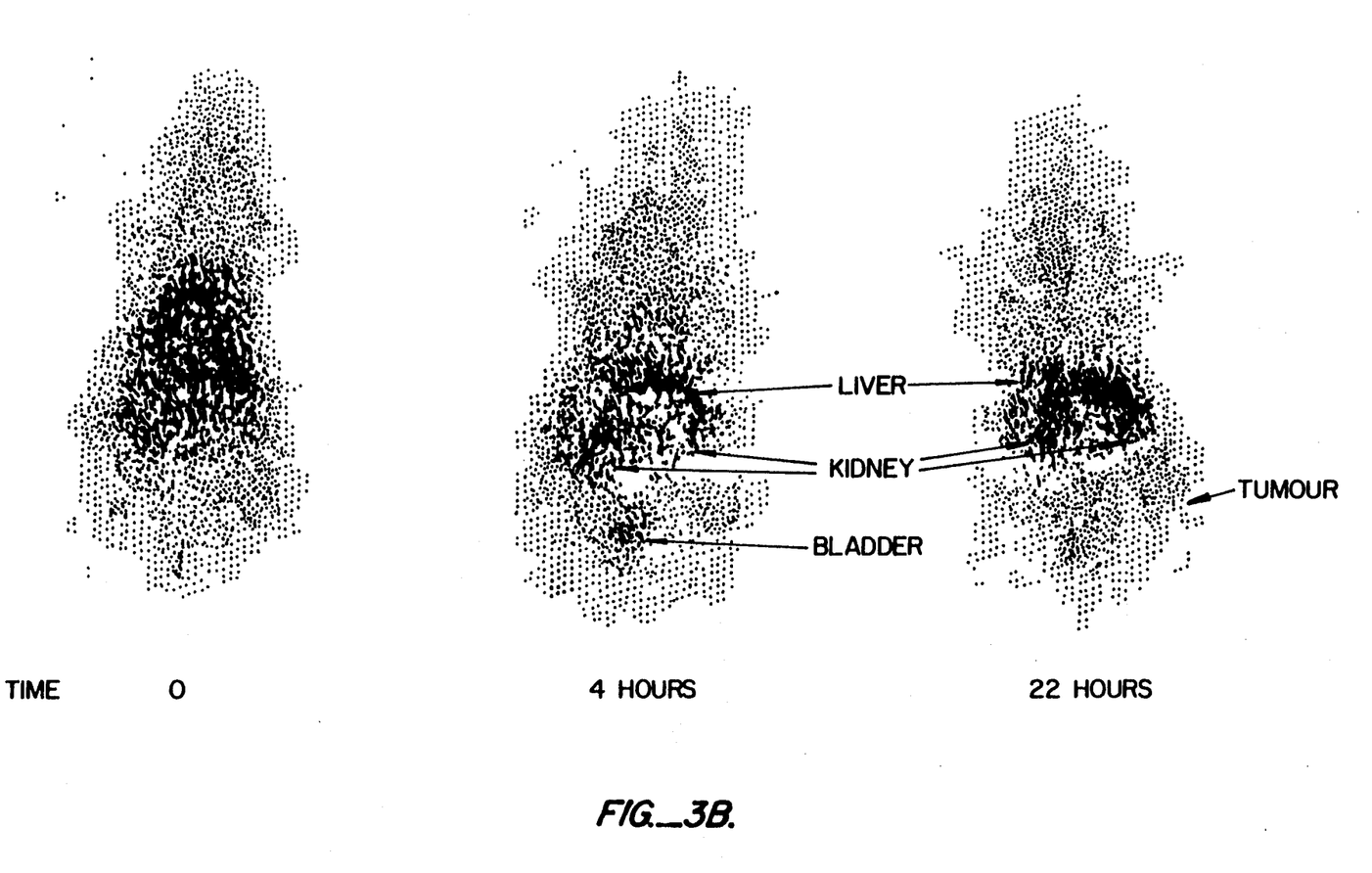

In mice given immunotoxin and MAN-HSA, the liver uptake was less marked on the images, and kidney uptake tended to dominate the views (FIG. 3b). Radioactivity was faintly visible in the tumour xenografts indicating a slight improvement in tumour uptake.

Quantification of radiolabel distribution in the images showed liver uptake rising to 70%–80% in mice not given MAN-HSA, with kidneys too poorly defined for accurate analysis. Tumour levels reached a maxim, in one mouse, of 35 of whole body radioactivity. The images of the mice with the MAN-HSA showed liver activity declining to background levels, but those of kidneys increasing to over 40% of the whole image count rate. ROI's around tumours showed up to 7% of the whole body radioactivity (Table I).

Figure 4:
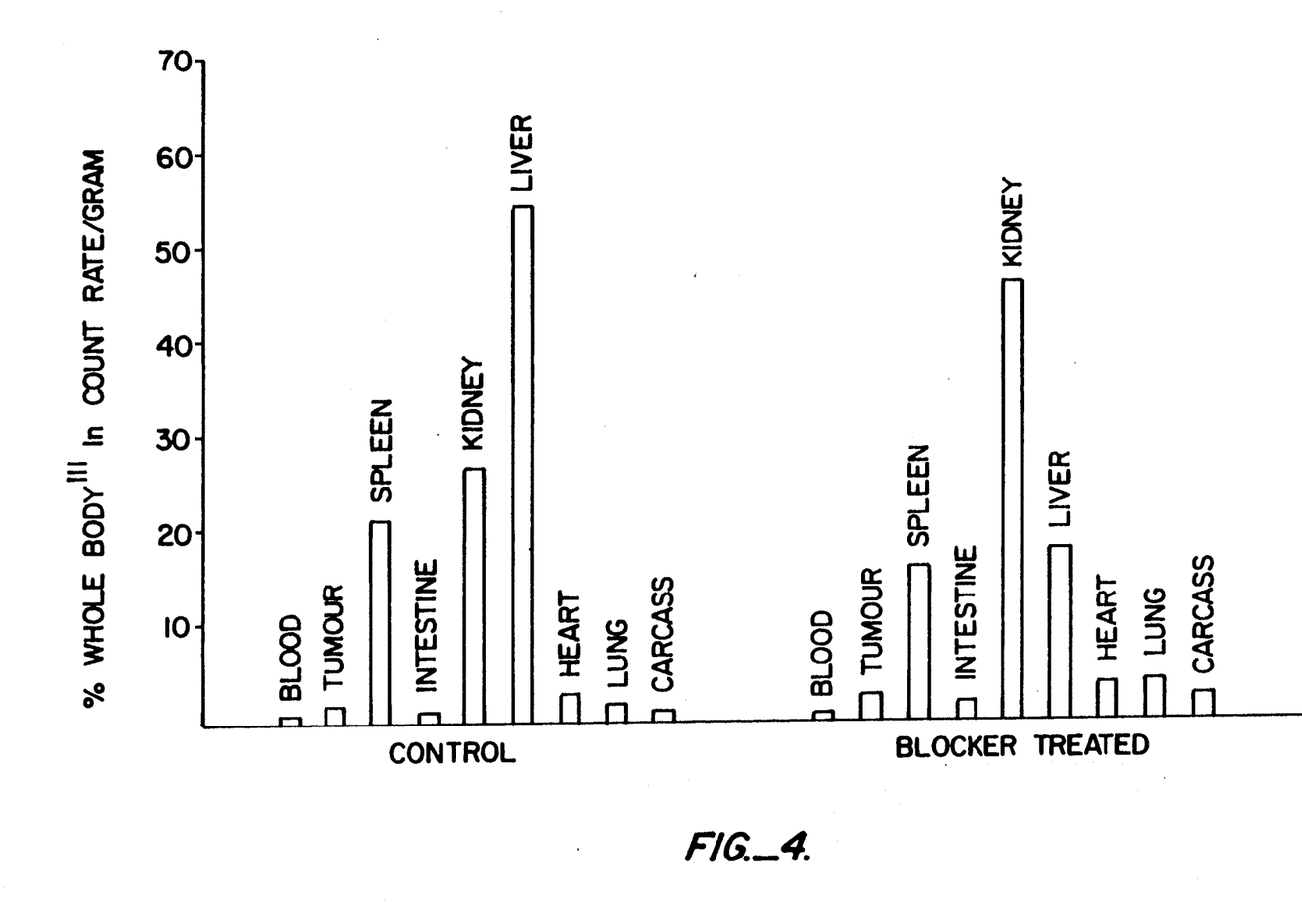
FIG. 4. Dissection analysis of mice treated with $^{111}$In-DTPA-RTA-(791/36).

Dissection analysis carried out after 48 hours with the mice not given MAN-HSA showed high liver, spleen and kidney uptake of radiolabel (FIG. 4). Tumour levels of $^{111}$In in 791T xenografts were relatively low with a mean value of 1.6% of the whole body radioactivity/gram. The mean blood level was 0.24% of the whole body radioactivity/g. Dissection analysis of tracer in the mice given $^{111}$In-immunotoxin and MAN-HSA showed reduced spleen and liver uptake compared with control mice, but increased kidney levels (FIG. 4). Tumour levels of $^{111}$In in 791T xenografts were marginally higher (2.5% of the whole body radioactivity/gram) than xenograft levels in mice not given hepatic blocker, but blood levels were also higher at 0.44% of the whole body radioactivity/gram. The mean whole body retention of $^{111}$In, expressed as a percentage of the injected radioactive dose, was 16% in the mice not given the hepatic blocking agent and 15% in the MAN-HSA treated mice.

From the data derived from the above work, it can be demonstrated that the labelled immunotoxins make possible monitoring of immunotoxin delivery to individuals on both a whole body level and on a specific organ level.

Although the present invention has been described in some detail by way of illustration and example for purposes of clarity and understanding, it will be apparent that certain changes and modifications may be practiced within the scope of the appended claims.

TABLE I

QUANTIFICATION FROM IMAGES OF THE BIODISTRIBUTION OF $^{111}$In LABELLED IMMUNOTOXIN

| Mouse No. | Blocking Agent | Time (Hours)[a] | Whole body radioactivity (%) in:- | | |
|---|---|---|---|---|---|
| | | | Liver | Kidneys | Tumors |
| 1 | — | 0 | 48 | N.Q.[b] | 1 |
| | | 6 | 71 | N.Q. | 1 |
| | | 24 | 71 | N.Q. | 1 |
| 2 | — | 0 | 57 | N.Q. | 3 |
| | | 6 | 66 | N.Q. | 3 |
| | | 24 | 81 | N.Q. | 3 |
| 3 | — | 0 | 55 | N.Q. | 1 |
| | | 6 | 68 | N.Q. | 1 |
| | | 24 | 70 | N.Q. | 2 |
| 4 | MAN-HSA[c] | 0 | 35 | N.Q. | 4 |
| | | 4 | 17 | 32 | 5 |
| | | 22 | N.Q. | 47 | 7 |
| 5 | MAN-HSA | 0 | 30 | N.Q. | 3 |
| | | 4 | N.Q. | 45 | 4 |
| | | 22 | N.Q. | 39 | 3 |
| 6 | MAN-HSA | 0 | 20 | N.Q. | 4 |
| | | 4 | N.Q. | 42 | 5 |
| | | 22 | N.Q. | 46 | 5 |

[a]Time after intravenous injection of immunotoxin
[b]N.Q.—not quantifiable. Count rate too low for ROI to be defined
[c]MAN-HSA—Mannosylated human serum albumin.

What is claimed is:

1. A method for in vivo radioimmunodetection of a cytotoxic immunotoxin comprising
administering internally to a mammal a radio-labeled immunotoxin, wherein a heterobifunctional chelating agent provides a chemical bridge between a radiolabel and a cytotoxic component bound to the antigen-binding component of said immunotoxin, and
detecting externally the distribution of said immunotoxin in the mammal.

2. A method of claim 1 wherein the bifunctional chelator is cyclic dianhydride of diethylenetriaminepentaacetic acid, or bromo acetamidobenzylethylenediaminetetraacetic acid.

3. The method of claim 1 wherein the cytotoxic portion of the immunotoxin is selected from the group consisting of toxic lectins and their derivatives, daunomycin, adriamycin, methotrexate and cytarabine.

4. A method of claim 1 wherein the radiolabel is a gamma emitter.

5. A method of claim 4 wherein the gamma emitter is $^{99}$Tc or $^{111}$In.

6. A method of claim 1 wherein the immunotoxin is comprised of an immunoglobulin specific for epitopes upon cell surface antigens wherein the epitopes are markers for a disease state.

7. The method of claim 6 wherein the epitopes are markers for cancer.

8. The method of claim 7 wherein the epitopes are located upon the 72,000 dalton cell surface glycoprotein associated with osteogenic sarcoma derived cells.

9. The method of claim 8 wherein the epitopes are bound by the antibodies secreted by the hybridoma line ATCC HB 9173.

10. The method of claim 7 wherein the epitopes are located upon the carcinogenic embryonic antigen.

11. The method of claim 10 wherein the epitopes are bound to by the antibodies secreted by the hybridoma line ATCC HB 9174.

12. The method of claim 1, wherein the antigen-binding component is an immunoglobulin.

13. An imaging agent comprising a radiolabeled immunotoxin, wherein a heterobifunctional chelating agent provides a chemical bridge between a radiolabel and a cytotoxic component bound to the antigen-binding component of said immunotoxin.

14. An imaging agent of claim 13 wherein the bifunctional chelator is cyclic dianhydride of diethylenetriaminepentaacetic acid, or bromoacetamidobenzylethylenediaminetetraacetic acid.

15. An imaging agent of claim 13 wherein the cytotoxic portion of the immunotoxin is selected from the group consisting of toxic lectins and their derivatives, daunomycin, adriamycin, methotrexate and cytarabine.

16. An imaging agent of claim 13 wherein the radiolabel is a gamma emitter.

17. An imaging agent of claim 16 wherein the gamma emitter is $^{99}$Tc or $^{111}$In.

18. An imaging agent of claim 13 wherein the immunotoxin is comprised of an immunoglobulin specific for epitopes upon cell surface antigens wherein the epitopes are markers for a disease state.

19. An imaging agent of claim 18 wherein the epitopes are markers for cancer.

20. The composition of claim 19 wherein the epitope is located upon the 72,000 dalton cell surface glycoprotein associated with osteogenic sarcoma derived cells.

21. The composition of claim 20 wherein the epitope is bound by the antibodies secreted by the hydridoma line ATCC HB 9173.

22. The composition of claim 19 wherein the epitope is located upon the carcinogenic embryonic antigen.

23. The composition of claim 20 wherein the epitope is bound to by the antibodies secreted by the hybridoma line ATCC HB 9174.

* * * * *